United States Patent
Howard et al.

(10) Patent No.: US 6,416,764 B1
(45) Date of Patent: *Jul. 9, 2002

(54) VACCINE

(75) Inventors: John Christopher Howard; Michael Cyril Clarke; John Brownlie, all of Compton (GB)

(73) Assignee: Vericore Limited, Lancaster (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/338,869

(22) Filed: Jun. 23, 1999

Related U.S. Application Data

(62) Division of application No. 08/605,274, filed on Feb. 7, 1996, now Pat. No. 6,291,228, which is a continuation of application No. 08/416,452, filed on Apr. 3, 1995, now abandoned, which is a continuation of application No. 08/279,272, filed on Jul. 22, 1994, now abandoned, which is a continuation of application No. 08/146,839, filed on Nov. 2, 1993, now Pat. No. 5,428,087, which is a continuation of application No. 07/998,777, filed on Dec. 24, 1992, now abandoned, which is a continuation of application No. 07/634,197, filed on May 7, 1991, now abandoned.

(30) Foreign Application Priority Data

Aug. 3, 1988 (GB) .............................................. 8818415
Aug. 3, 1989 (WO) ................................ PCT/GB89/00882

(51) Int. Cl.$^7$ ........................ A61K 39/12; A01N 65/00; A01N 63/00; C12N 5/02; C12N 7/08

(52) U.S. Cl. .................. 424/218.1; 424/93.1; 424/93.2; 424/93.6; 435/235.1; 435/236; 435/325; 435/237

(58) Field of Search .............................. 424/9.2, 184.1, 424/202.1, 218.1, 221.1, 278.1, 93.1, 93.2, 93.6; 435/5, 235.1, 236, 231, 325

(56) References Cited

U.S. PATENT DOCUMENTS

| | | |
|---|---|---|
| 3,122,477 A | 2/1964 | Beckenhauer et al. ........ 167/80 |
| 3,293,129 A | 12/1966 | Baker ......................... 167/78 |
| 3,346,456 A | 10/1967 | Baker ......................... 167/80 |
| 3,577,525 A | 5/1971 | Baker ......................... 424/89 |
| 3,838,004 A | 9/1974 | Mebus et al. ................ 195/1.3 |
| 3,839,556 A | * 10/1974 | Mebus et al. ................ 424/89 |
| 3,869,547 A | 3/1975 | Mebus et al. ................ 424/89 |
| 3,873,422 A | 3/1975 | Mebus ....................... 195/1.3 |
| 3,914,408 A | 10/1975 | Mebus ....................... 424/89 |
| 3,919,044 A | 11/1975 | Melnick et al. .............. 195/1.5 |
| 3,919,412 A | 11/1975 | Mebus ....................... 424/89 |
| 3,919,413 A | 11/1975 | Mebus ....................... 424/89 |
| 3,925,544 A | 12/1975 | Sheckmeister et al. ....... 424/89 |
| 4,618,493 A | 10/1986 | Delgoffe et al. ............. 424/89 |
| 4,714,678 A | 12/1987 | Delgoffe et al. ............ 435/235 |
| 4,806,350 A | 2/1989 | Gerber ....................... 424/88 |
| 4,900,549 A | 2/1990 | De Vries et al. ............. 424/88 |

FOREIGN PATENT DOCUMENTS

| | | |
|---|---|---|
| EP | 0 106 831 | 4/1984 |
| EP | 0 109 942 A2 | 5/1984 |
| EP | 0 208 507 | 1/1987 |
| EP | 0 231 039 B1 | 8/1987 |
| EP | 0 436 620 B1 | 7/1991 |
| GB | 992330 | 5/1965 |
| GB | 1023526 | 3/1966 |
| GB | 1 401 565 | 7/1975 |
| GB | 1402565 | 7/1975 |
| GB | 1560344 | 2/1980 |
| GB | 2079786 A | 1/1982 |
| JP | 48-2766 | 1/1973 |
| JP | 55-31058 | 3/1980 |

OTHER PUBLICATIONS

US 6,156,559, 12/2000, Howard (withdrawn)
McClurkin et al. 1978. Selected isolates of bovine viral diarrhea (BVD) virus propagated on bovine turbinate cells: virus titer and soluble antigen production as factors in immnogenicity of killed BVD virus. Archives of Virology. vol. 58, pp. 119–125.*
Pocock et al. 1987. Variation in the intracellular polypeptide profiles from different isolates of bovine virus diarrhea virus. Archives of Virology. Vo. 94 (1–2), pp. 45–53. Abstract only.*
Morein. 1987. Potentiation of the immune response by immunization with antigens in defined multimeric physical forms. Veterinary Immunology and Immunopathology. vol. 17, pp. 153–159.*
Howard et al. 1987 Comparison by the neutralisation assay of pairs of non–cytopathogenic and cytopathogenic strains of bovine virus diarrhoea virus isolated fromn cases of mucosal disease. Veterinary Microbiology. vol. 13 (4), pp. 361–369. Abstract only.*
Comment "BVDV: breaking the cycle of infection," *The Veterinary Record*, Jul. 15, 1995, p. 53.
Vaccination–challenge Experiments Table, 1 sheet.
"Vaccination Helps Cut Fertility Costs," *Dairy Farmer*, Jul. 1, 1998, 1 sheet.
"Bovidec® Controlling BVD Infertility," C–Vet, 3 sheets.
"Triangle 1—Bovine Virus Diarrhea Vaccine," Fort Dodge, 2 sheets.
"Bovine Viral Diarrhoea," *OIE Manual*, 1996, Chapter X.5. Not In the Code, pp. 651–659.
Barei, S. et al., "Comparison of the Potency of Cattle of Trivalent FMD Caccines Adjuvanted by Aluminum Hydroxide–Saponin or Oil Emulsion," *Zbl. Vet. Med. B.*, 26 (1979) pp. 464–460.

(List continued on next page.)

*Primary Examiner*—James Housel
*Assistant Examiner*—Shannon A. Foley
(74) *Attorney, Agent, or Firm*—Crompton, Seager & Tufte, LLC

(57) ABSTRACT

A vaccine comprises a non-cytopathogenic strain of bovine viral diarrhea virus, grown in a bovine derived cell line such as MDBK and killed, for example with β-propiolactone. The adjuvant is Quil A.

9 Claims, No Drawings

OTHER PUBLICATIONS

Bates, Andrew, "Light at the End of the Tunnel," *BCVA Congress Times*, Apr. 22, 1998, pp. 1–2.

Bittle, J.L. et al., "Carriers and Adjuvants for Chemically Synthesized Antigens," *Advances in Carriers and Adjuvants for Veterinary Biologics*, (1986) 1$^{st}$ Edition, pp. 151–156.

Brownlie, J. et al., "Experimental Infection of Cattle in Early Pregnancy with a Cytopathic Strain of Bovine Virus Diarrhoea Virus," *Research in Veterinary Science*, 1989, 46, pp. 307–311.

Brownlie, J. et al., "Experimental Production of Fatal Mucosal Disease in Cattle," *The Veterinary Record* Jun. 2, 1984, pp. 535–536.

Brownlie, J. et al. "Pathogenesis and Epidemiology of Bovine Virus Diarrhoea Virus Infection of Cattle," *Ann Rech Vet*, 1987, 18, pp. 157–166.

Brownlie, J. et al., Protection of the Bovine Fetus from Bovine Viral Diarrhoea Virus by Means of a New Inactivated Vaccine, *The Veterinary Record*, Jul. 15, 1995, pp. 58–63.

Brownlie, J. et al., "Scientific Reports: Cattle—Mucosal Disease," Annual Report of the Institute for Animal Health, 1987, p. 20.

Brownlie, Joe, "Clinical Aspects of the Bovine Virus Diarrhoea/Mucosal Disease Complex in Cattle," *In Practice*, Nov. 1985, pp. 195–202.

Browlie, Joe, "The Pathways for Bovine Virus Diarrhoea Virus Biotypes in the Pathogenesis of Disease," *Arch Virol*, 1991, Suppl. 3, pp. 79–96.

Corapi, Wayne V. et al., "Monoclonal Antibody Analysis of Cytopathic and Noncytopathic Viruses from Fatal Bovine Viral Diarrhea Virus Infections," Journal of Virology, Aug. 1988, pp. 2823–2827.

Dalsgaard K., et al., Vaccination of Pigs Against Hog Cholera (Classic Swine Ferer) with a Detergent Split Vaccine, *Acta. vet. scan.*, (1976) 17, 465–474.

Dalsgaar, Kristian et al., "Classical and New Approaches to Adjuvant Use in Domestic Food Animals," *Advances in Veterinary Science and Comparative Medicine*, (1990) vol. 35, pp. 121–160.

Dalsgaard, Kristian, "Saponin Adjuvants," *Archive für die gesamte Virusforschung*, (1974) 44, pp. 243–254.

Dalsgaard, Kristian, "A Study of the Isolation and Characterization of the Saponin Quil A," *Acta. Vet. Scand.* (1978) 19, suppl. 69, pp. 7–39.

Eskildsen, M. et al., "Serological Diagnosis of Classical Swine Fever," *Acta. vet. scand.* (1976) 17, pp. 131–141.

Fernelius et al., "Evaluation of β–Propiolactone–Inactivated–and Chloroform–Treated–Virus Vaccines Against Bovine Viral Diarrhea–Mucosal Disease," *Am. J. Vet. Res.*, Jul. 1972 vol. 33, No. 7, pp. 1421–1431.

Harkness, J.W. et al., et al., "The Efficacy of an Experimental Inactivated BVD–MD Vaccine," Commission of the European Communities Seminar, Sep. 1985, pp. 233–251.

McClurkin, A. W. et al., "Evaluation of Acetylethylene–imine–killed Bovine Viral Diarrhea—Mucosal Disease Virus (BVD) Vaccine for Prevention of BVD Infection of the Fetus," *Proc. U.S. Animal Health Assoc.*, (1975) 79, pp. 114–123.

McClurkin, A. W. et al., "Selected isolates of Bovine Viral Diarrhea (BVD) Virus Propagated on Bovine Turbinate Cells: Virus Titer and Soluble Antigen Production as Factors in Immunogenicity of Killed BVD Virus," *Archives of Virology*, (1978) 58, pp. 119–125.

Meyling et al, "Experimental Exposure of Vaccinated and Non–Vaccinated Pregnant Cattle to Isolates of Bovine Viral Diarrhoea Virus (BVD)," EC Seminar on Pestiviruis Infection of Ruminants Sep. 1985, pp. 225–232.

Milton, "More on Mucosal Disease," *The Veterinary Record*, Comment, vol. 114, No. 22, Jun. 2, 1984.

Morein, B. et al., "Potentiation of the Immune Response by Immunization with Antigens in Defined Multimeric Physical Forms," *Veterinary Immunology and Immunopathology*, 17, (1987) pp. 153–159.

Morgan, D.O. et al., "Vaccination Against Foot–and–Mouth Disease," *New Developments with Human and Veterinary Vaccines*, (1980) pp. 169–178.

Morzaria, S.P., "A Field Trial with a Multicomponent Inactivated Respiratory Viral Vaccine," *The Veterinary Record*, Nov. 3, 1979, pp. 410–414.

Neaton, H.J., *Veterinary Medicine*, 81, Sep. 1986 pp. 876–881.

Stern, Elizabeth, "Viral Complex Threatens Cattle in the UK," *Livestock Farming*(1987) 25, p. 30.

Stewart–Tull, Duncan et al., "Use of Mineral Hydrocarbons in Human and Veterinary Vaccines," date unknown, 11 sheets.

Stott, E.J. et al., "Development of a Potent Inactivated Vaccine Against Respiratory Syncytial Virus Infection of Calves," Proceeding of the 14 World Congress of Diseases of Cattle, (1986) pp. 669–674.

Stott, E.J. et al., "Preliminary Observations on 'Quil–A' as an Adjuvant for an Inactivated Respiratory Syncytial Virus Vaccine," Report and Proceedings from Symposium on Vaccine Adjuvants held in London on the Mar. 30, 1981, Nov. 1981, pp. 19–24.

Sutmoeller, P. et al., *The FMD Vaccine Situation in South America*, pp. 304–321.

Tsretkov, et al., "Production and Study of the Immunogenic Properties of a Bivalent Activated Vaccine Against Mucosal Disease," *Vet. Med. Nauki*, (1979) 16, pp. 3–9 (abstract only).

Zwetkow, P. et al., "Investigation on the Immunogenity of concentrated Ethanol Saponin Vaccine Against Mucosal Disease—Bovine Viral Diarrhea," From the Veterinary Institute of Immunology Sofia.

\* cited by examiner

VACCINE

RELATED APPLICATIONS

This application is a divisional application of U.S. patent application Ser. No. 08/605,274, filed Feb. 7, 1996; now U.S. Pat. No. 6,291,228 which is a continuation of U.S. patent application Ser. No. 08/416,452, filed Apr. 3, 1995 now abandoned; which is a continuation of U.S patent application Ser. No. 08/279,272, filed Jul. 22, 1994, now abandoned; which is a continuation of U.S. patent application Ser. No. 08/146,839, filed Nov. 2, 1993, now U.S. Pat. No. 5,428,087 which is a continuation of U.S. patent application Ser. No. 07/998,777, filed Dec. 24, 1992, now abandoned; which is a continuation of U.S. patent application Ser. No. 07/634,197, filed May 7, 1991, now abandoned.

Bovine virus diarrhoea virus (BVDV) is extremely common in cattle in the UK, the remainder of Western Europe, North America, Australia and Africa. Infection with this virus may result in a variety of syndromes and pathologies influenced largely by the age of animals when first infected. In young, previously uninfected calves the virus causes a transient infection. This is associated with leucopenia, and an interrelated period of immunosuppressive and increased susceptibility to infection with other microorganisms. BVDV is, after RSV (respiratory syncitial virus), probably the most important virus associated with outbreaks of respiratory disease in young housed calves and because of its immuno-suppressive effect it may be involved in other calf infections, for example enteritis. This virus is also considered to be a major contributor to disease in "feedlot calves" in the USA and Canada. Following recovery, animals exhibit a degree of immunity to reinfection. However, this immunity appears not to be absolute or lifelong.

More serious problems result from infection of pregnant cattle. Abortion may ensure or alternatively deformities may be produced in the foetus that is carried to term; these deformities may result from exposure to virus at the time when immunocompetence is developing and could be the result of an incomplete immune response. Infection of the feotus before immunocompetence develops can result in the foetus remaining viraemic through the period of gestation and the subsequent birth of a calf that remains persistently viraemic, with a non-cytopathogenic form of the virus, and specifically immunotolerant to BVDV for life. Such calves are the animals that die later of mucosal disease; an event triggered by superinfection with a cytopathogenic variant of BVDV.

It has been estimated that about 0.4% of apparently normal beef calves in the UK are viraemic and these animals represent a major source of infection on farms.

Traditionally, viral vaccines fall into two classes: live vaccines containing live viruses which have been treated or grown (attenuated) in such a way as to make them less pathogenic, and vaccines containing killed (inactivated) virus particles. In the context of BVDV, the viruses themselves may be cytopathogenic or non-cytopathogenic. Thus, in principle, four main classes of BVDV vaccine could exist, although the vast majority of commercial vaccines are based on the cytopathogenic virus. Moreover, it is thought by many that live vaccines are unacceptable because live cytopathogenic vaccine strains may produce death from mucosal disease in persistently viraemic animals, and live non-cytopathogenic virus vaccine may infect the foetus in pregnant cattle and result in any of the diseases outlined above.

Infection via the respiratory tract is probably the most important route of transmission of the virus on farms and protection against spread via this route would be expected to have a major beneficial effect in controlling disease due to BVDV.

Parenteral vaccination with inactivated BVDV protected against respiratory infection. In one experiment all of 5 vaccinated calves were resistant to respiratory challenge and all of 5 controls become infected.

The killed BVDV antigens tested induced the production of high titres of neutralising antibodies. These were shown to rise from less than 50 before vaccination to greater than or equal to 2,000–10,000 units after vaccination.

The present invention provides a vaccine comprising a killed, non-cytopathogenic virus, wherein the virus is grown on a cell line which is derived from bovine cells such as the MDBK cell line (Madin Darby Bovine Kidney; Madin & Darby (1958); available from ECACC, Salisbury, Wiltshire, UK) and is adjuvanted with Quil A. MDBK cells are available in many laboratories throughout the world. Other bovine cell lines useful in the practice of the invention include EBL cells, NM5 cells, LWC874 cells and CTe cells.

The MDBK cell line is preferably used at passage levels 147–187, more preferably at pass 147 to 157 and most preferably at pass 147. Seed virus is preferably prepared by adding about $10^6$ $TCD_{50}$ of BVDV (non-cytopathogenic strain) to confluent cultures of calf testis cells. Calf testis cells are preferred to grow the seed culture because virus yields are higher in these cells, whereas yields of antigen are greater in MDBK cells. The cells may be grown in roller bottles with Eagles's MEM medium and added foetal bovine serum 7.5%, sodium bicarbonate 0.11% and lactalbumin hydrolysate 0.25%. After addition of the virus, the culture may be maintained with 50 ml medium; Eagle's BME with foetal bovine serum 2%, sodium bicarbonate 0.17%, lactalbumin hydrolysate 0.25% and magnesium chloride hexahydrate 0.6%. The culture may be incubated at about 36° C. for 5 to 9 days, preferably 7 days, and then subjected to a single cycle of freeze/thaw. The suspension may be centrifuged at about 500 g for 4 to 6 minutes, preferably 5 minutes, to remove gross debris and the supernatant fluid stored in small volumes, ready for use, at about −70° C. The titre of the stored seed virus may be determined by assay in cultures of calf testis cells.

Virus antigen is prepared by adding about 1 ml of seed virus, containing about $10^6$ $TCD_{50}$ of BVDV, to cultures of MDBK cells. These cells may be grown in roller bottles with Eagle's MEM, foetal bovine serum 10% and sodium bicarbonate 0.11% and are used after about 4 days' growth when the cultures are about 75% confluent. After addition of the virus the culture may be maintained with 125 ml of BME medium (vide supra). Seven days later when the culture contains about $10^8$ cells and a virus titre of about $10^{8.5}$ $TCD_{50}$, β-propiolactone is added to a concentration of 1 in 500 and the bottle rolled for 3 hours at 36° C. to inactivate the virus. Complete inactivation of the antigen preparation is checked by passage of samples in cultures of calf testis cells. The antigen is stored at −20° C.

Before cell cultures are used for the preparation of seed virus and virus antigen they are checked for the presence of adventitious BVDV. Foetal bovine serum is checked for freedom from virus and BVDV antibody.

One dose of the vaccine is prepared by mixing 1 mg of "Quil A" (Superfos A/S Denmark) as 50 ul of a stock (20 mg/ml in water) to 4 ml of beta-propiolactone-inactivated virus. This is injected subcutaneously behind the shoulder of calves, aged about 3 months and shown to be free of BVDV antibody, either maternally derived or produced as a result of infection.

Vaccinated calves showed an antibody response (Table 1), determined by ELISA (Howard, Clarke & Brownlie, 1985), which was detected 6 weeks after the first vaccination. These animals and unvaccinated controls were challenged with a strain of BVDV (11249nc) selected because of its tropism for the respiratory tract and consistent rate of nasopharyngeal shedding. Calves were infected intranasally on week 8. Virus shedding was determined by examination of naso-pharyngeal swabs (blood was also tested) for up to 10 days after challenge and samples were assayed in cultures of calf testis cells. BVDV was recovered from the control animals (Tables 2,3) but not the vaccinated group. The relationship, for individual animals, between antibody levels at the time of challenge and the susceptibility to infection is shown in Table 3. None of the controls had detectable antibody at the time of challenge and they all became infected and seroconverted (Table 1).

BVDV antigen may be included with other microorganisms (preferably inactivated) to form a multivalent vaccine. Suitable organisms include respiratory syncytial virus, parainfluenza 3 virus and *Mycoplasma bovis*.

Instead of using whole virus, it may be advantageous to separate the antigens from the virus and to use them with Quil A and, optionally, suitable carriers and the like. This may be achieved by known means.

TABLE 1

Antibody responses by ELISA[1] in calves vaccinated with strain Ky1203nc

| Group | No. of Calves | week[2] | | | | |
|---|---|---|---|---|---|---|
| | | 0 | 3 | 6 | 8 | 10 | 12 |
| Non-vaccinated | 5 | 1.4 | ND | ND | 1.4 | 2.09+0.60 | 2.50+0.12 |
| Vaccine standard dose | 5 | 1.4 | 1.4 | 3.07+0.30 | 3.52+0.13 | 4.38+0.25 | 4.09+0.29 |

[1]mean number of units of antibody ($10^n$) ± SD
[2]calves vaccinated on weeks 0, 3 and 6; challenged on week 8 with strain 11249nc intransally.

TABLE 2

Effect of vaccination with strain Ky1203nc on infection with BVDV

| Group | No. of Calves | No. of calves infected[1] on indicated day | | | | |
|---|---|---|---|---|---|---|
| | | 0 | 4 | 6 | 8 | 10 |
| Non-vaccinated | 5 | 0 | 1 | 5 | 1 | 0 |
| Vaccine-standard dose | 5 | 0 | 0 | 0 | 0 | 0 |

[1]Isolations from nasopharyngeal swabs

TABLE 3

Relationship between antibody at time of challenge and susceptibility to infection in individual animals

| Animal Code No. | Vaccine[1] | Antibody[2] | Virus isolation[3] | | Leucopenia %[4] |
|---|---|---|---|---|---|
| | | | N. Ph. swab | Blood | |
| X502 | S | 3.71 | − | − | 5 |
| A21 | S | 3.57 | − | − | 0 |
| X694 | S | 3.51 | − | − | 0 |
| X657 | S | 3.42 | − | − | 0 |
| X684 | S | 3.38 | − | − | 5 |
| A10 | — | 1.4 | + | − | 46 |
| A407 | — | 1.4 | + | + | 48 |
| X192 | — | 1.4 | + | + | 53 |
| X658 | — | 1.4 | + | + | 52 |
| X659 | — | 1.4 | + | + | 54 |

[1]Animals given standard dose (S), or no vaccine (—)
[2]Units of antibody ($10^n$) by ELISA on day of challenge, animals arranged in decreasing order
[3]Isolations from nasopharyngeal swab as in Table 2, isolations from blood on day 6
[4]Percentage reduction in cell count, compared to average of 3 preinoculation values The MDBK (Madin-Darby Bovine Kidney) cell line has been available for about 25 years from the American Type Culture Collection, Rockville, Md., USA as ATCC CCL 22. Since 1982, this line has been BVD-free. The same cell line has also been available from the European Collection of Animal Cell Cultures, Porton Down, Salisbury, Wiltshire, UK, as has MDBK from another source, under the accession number ECACC No. 85102401. A sample of the latter deposit has now been deposited with ECACC under the Budapest Treaty, with the date of Aug. 2nd, 1989 and the accession number 89080201.

What is claimed is:

1. A process for preparing a vaccine comprising the steps of (a) inoculating a cell line derived from bovine cells with a non-cytopathogenic bovine viral diarrhoea virus (BVDV), (b) growing said virus in the inoculated cells, (c) inactivating virus from step (b), and (d) admixing material from step (c) with Quil A.

2. A vaccine prepared according to the process of claim 1.

3. A process according to claim 1 wherein the inactivated virus comprises whole viruses.

4. A vaccine prepared according to the process of claim 3.

5. A process according to claim 1 wherein the cell line is inoculated with BVDV grown in calf testis cells.

6. A process according to claim 5 wherein the inactivated virus comprises whole viruses.

7. A vaccine prepared according to the process of claim 5.

8. A vaccine effective against bovine viral diarrhoea virus (BVDV) infections, comprising inactivated non-cytopathogenic BVDV grown in a cell line derived from bovine cells and Quil A as an adjuvant therefor.

9. A vaccine effective against bovine viral diarrhoea virus (BVDV) infections comprising inactivated non-cytopathogenic BVDV and Quil A as an adjuvant therefor.

\* \* \* \* \*

UNITED STATES PATENT AND TRADEMARK OFFICE
CERTIFICATE OF CORRECTION

PATENT NO.    : 6,416,764 B1
DATED         : July 9, 2002
INVENTOR(S)   : John C. Howard et al.

It is certified that error appears in the above-identified patent and that said Letters Patent is hereby corrected as shown below:

<u>Title page, Item [54] and Column 1, line 1,</u>
Title, delete "VACCINE" and insert therefor -- VACCINES AND PROCESSES FOR PREPARING THE SAME --.

Signed and Sealed this

Nineteenth Day of November, 2002

*Attest:*

*Attesting Officer*

JAMES E. ROGAN
*Director of the United States Patent and Trademark Office*